Figure 1:
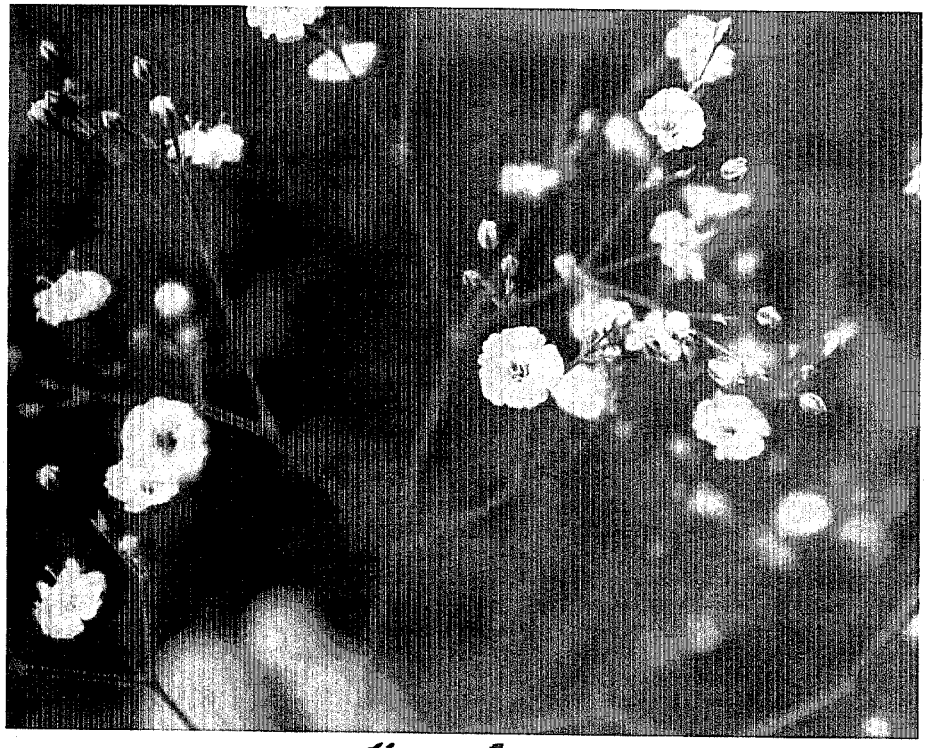

US00PP09164P

United States Patent [19]

Dehan

[11] Patent Number: Plant 9,164

[45] Date of Patent: Jun. 13, 1995

[54] GYPSOPHILA PLANT NAMED 'MAGIC GILBOA'

[75] Inventor: Klara Dehan, Holon, Israel

[73] Assignee: Danziger-"Dan" Flower Farm, Post Beit Dagan, Israel

[21] Appl. No.: 321,602

[22] Filed: Oct. 11, 1994

[51] Int. Cl.[6] ..... A01H 5/00

[52] U.S. Cl. ..... Plt./68.1

[58] Field of Search ..... Plt. 68.1

*Primary Examiner*—James R. Feyrer

[57] ABSTRACT

A distinct cultivar of Gypsophila plant named Magic Gilboa, characterized by its pure white flowers that are arranged in double rows; large number of flowers per lateral stem; storng and straight stems; requirement for only a 12 to 13-hour daylength to initiate and develop flowers; yield of a large number of cut flowers; and exceptional vase life.

1 Drawing Sheet

The present invention relates to a new and distinctive cultivar of Gypsophila, botanically known as *Gypsophila paniculata*, and hereinafter referred to by the cultivar name Magic Gilboa.

The new cultivar was developed by me in a controlled breeding program at Danziger — "Dan" Flower Farm, Mishmar Hashiva, Israel, by crossing the female, or seed, parent identified as *Gypsophila paniculata* selection DAN-8822 with the male, or pollen, parent identified as *Gypsophila paniculata* selection DAN-9056. Both parents are nonpatented selections developed by me in a controlled breeding program and used only as breeding parents.

Asexual reproduction of the new cultivar by terminal cuttings taken by me at Mishmar Hashiva, Israel, has shown that the combination of features of this new Gypsophila are firmly fixed and retained through successive generations of asexual reproduction.

The following characteristics are repeatedly observed and are determined to be the distinctive and unique characteristics of Magic Gilboa. These characteristics in combination distinguish Magic Gilboa from both its parent varieties and other cultivated Gypsophilas used in the floriculture industry:

1. Plants of the cultivar Magic Gilboa have pure white flowers that are arranged in double rows.
2. Plants of the cultivar Magic Gilboa produce an exceptionally large number of flowers per lateral stem.
3. Plants of the cultivar Magic Gilboa produce many strong and straight stems.
4. Plants of the cultivar Magic Gilboa only require a 12 to 13-hour daylength to initiate and develop flowers.
5. Plants of the cultivar Magic Gilboa yield a large number of cut flowers.
6. Plants of the cultivar Magic Gilboa produce fresh cut flowering stems that have exceptional vase life.

The new cultivar is most similar to the cultivar Magic Golan which was developed by me in a controlled breeding program at Danziger — "Dan" Flower Farm, Mishmar Hashiva, Israel. Magic Gilboa differs from Magic Golan in the following traits:

1. Leaves of plants of the cultivar Magic Gilboa are shorter and narrower than leaves of plants of the cultivar Magic Golan.
2. Stems of plants of the cultivar Magic Gilboa are shorter, smaller in diameter, lighter in fresh weight, and have shorter internodes than stems of plants of the cultivar Magic Golan.

3. Plants of the cultivar Magic Gilboa produce more lateral stems per plant compared to plants of the cultivar Magic Golan.
4. Flowers of plants of the cultivar Magic Gilboa are smaller, have fewer petals, and are slower to develop and open than flowers of the cultivar Magic Golan.
5. Plants of the cultivar Magic Gilboa produce more flowers per lateral stem compared to plants of the cultivar Magic Golan.

In comparison, plants of the cultivar Magic Gilboa are shorter, denser in plant form, and more floriferous than plants of the cultivar Magic Golan which are taller, more open in plant form, and less floriferous.

The new cultivar is also similar to the nonpatented *Gypsophila paniculata* cultivar Bristol Fairy in flower color. Magic Gilboa differs from Bristol Fairy in the following traits:

1. Plants of the cultivar Magic Gilboa have larger flowers than plants of the cultivar Bristol Fairy. Flowers are 1 mm larger in diameter on plants of Magic Gilboa compared to plants of Bristol Fairy.
2. Plants of the cultivar Magic Gilboa produce longer stems than plants of the cultivar Bristol Fairy. Stems are straighter and stronger on plants of Magic Gilboa compared to stems of plants of Bristol Fairy.
3. Leaves and stems of plants of the cultivar Magic Gilboa are more glabrous and glaucous than leaves and stems of plants of the cultivar Bristol Fairy.
4. Plants of *Gypsophila paniculata* usually initiate and develop flowers when the length of the day is longer than the length of the night. Plants of the cultivar Magic Gilboa will initiate and develop flowers when the length of the day is 12 to 13 hours, whereas plants of the cultivar Bristol Fairy require 16 hours for flower initiation and development.
5. The number of harvestable flowering stems of plants of the cultivar Magic Gilboa is more than twenty percent greater than the number of harvestable flowering stems of plants of the cultivar Bristol Fairy during times of high production, that is, from late spring to fall in the Northern Hemisphere.

Figure 2:
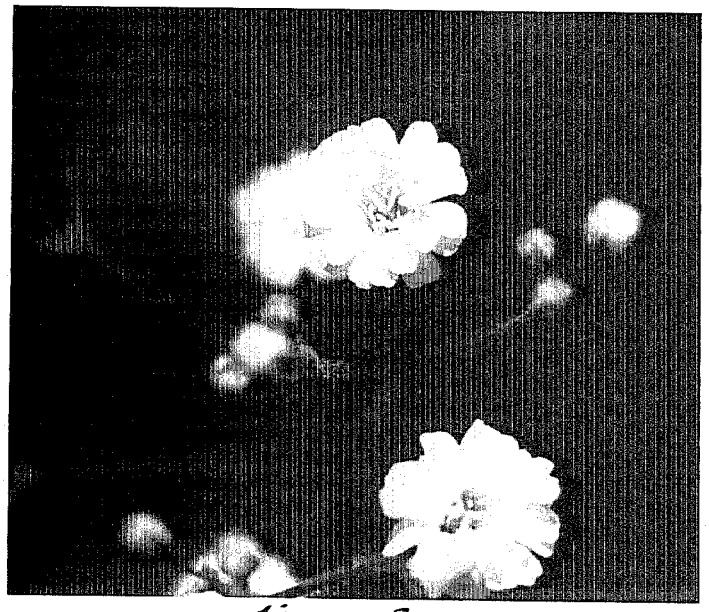

The accompanying colored photographs illustrate the overall appearance and flower color of the new cultivar, showing the colors as true as it is reasonably possible to obtain in colored reproductions of this type. The first photograph (FIG. 1) constitutes a typical harvested stem of Magic Gilboa. The second photograph (FIG. 2) is a close-up of an individual flower of Magic Gilboa.

In the following description, color references are made to The Royal Horticultural Society Colour Chart except where general terms of ordinary dictionary significance are used. The following observations, measurements and comparisons describe plants grown in Mishmar Hashiva, Israel, under normal commercial practice in a polyethylene-covered greenhouse with minimum night temperatures of 16° C. and maximum day temperatures of 20° to 30° C. during the summer. Magic Gilboa has not been observed under all possible environmental conditions. The phenotype may vary significantly with variations in environment such as temperature, light intensity and daylength.

Botanical classification:

*Gypsophila paniculata* cultivar Magic Gilboa.

Commercial use:

Fresh or dried cut flower.

Parentage:

*Female (seed) parent.*—*Gypsophila paniculata* selection DAN-8822.

*Male (pollen) parent.*—*Gypsophila paniculata* selection DAN-9056.

Propagation:

A. *Type.*—Terminal tip cuttings.

B. *Time to initiate roots.*—10 days at 25° C.; 15 days at 20° C.

C. *Rooting habit.*—Fibrous and well-branched.

Plant description:

A. *General appearance.*—Spreading and robust, diffusely branched perennial, lateral stems harvested as fresh or dried cut flowers, flowers arranged in panicles.

B. *Foliage description.*—1. Leaf shape: Linear-lanceolate with acute tip. 2. Leaf size: a. Maximum length: 10 cm. b. Maximum width 1.5 cm. 3. Leaf texture: Glabrous and glaucous. 4. Leaf margin: Entire. 5. Color: Young foliage, upper surface: 147A. Young foliage, under surface: 137A. Mature foliage, upper surface: 147A. Mature foliage, under surface: 137A. 6. Venation: Parallel.

C. *Lateral stem description.*—1. Internode length: On average 4.5 cm. 2. Color: 147A to 147B. 3. Quantity (yield): 10 to 12 lateral stems per plant. 4. Texture: Glabrous and glaucous. 5. Length: 0.9 to 1.1 m. 6. Diameter: 6 to 7 mm. 7. Fresh weight: 30 to 40 g. 8. Strength: Very strong and solid.

Flowering description:

A. *Flowering habit.*—Freely flowering.

B. *Natural flowering season.*—In the Northern Hemisphere, flowering occurs from spring until fall or under long day conditions. In Israel during the summer, plants flower 7 weeks after planting; and during winter, plants flower 13 weeks after planting.

C. *Flowers borne.*—Flowers arranged in a loose panicle.

D. *Quantity of inflorescences.*—Very floriferous; usually 1800 to 2000 flowers per lateral stem.

E. *Flower opening rate.*—From flower bud formation, flowers are fully open after 12 to 14 days depending on temperature and light intensity.

F. *Cut flower longevity.*—At least 3 weeks.

G. *Flower size.*—8 to 9 mm in diameter.

H. *Petals.*—1. Shape: Semi-circular with toothed abaxial margin. 2. Size: a. Height: 3 mm. b. Width: 3.5 mm. 3. Quantity: 46 per flower arranged in double rows. 4. Color: a. When opening: 155D. b. Upper surface: 155D. c. Under surface: 155D. d. Fading to: 155C.

I. *Flower bud.*—1. Shape: Round. 2. Color: 138C.

J. *Reproductive organs.*—1. Androecium: a. Stamen number: 10. b. Anther shape: Filamentous. c. Anther color: 155D. d. Pollen color: 155D. 2. Gynoecium: a. Stigma color: 144A. b. Style number: 2. c. Style color: 144c. d. Ovary: 5-celled. e. Ovary color: 144C. f. Ovary size: 1 to 2 mm.

Disease resistance: No fungal or bacterial problems observed.

Seed development: Seed production is very rarely observed.

I claim:

1. A new and distinct cultivar of Gypsophila plant named Magic Gilboa, as illustrated and described.

* * * * *